US010642067B2

(12) United States Patent
Brennan et al.

(10) Patent No.: US 10,642,067 B2
(45) Date of Patent: May 5, 2020

(54) AMETROPIA TREATMENT TRACKING METHODS AND SYSTEM

(71) Applicant: Johnson & Johnson Vision Care, Inc., Jacksonville, FL (US)

(72) Inventors: Noel A. Brennan, Jacksonville, FL (US); Khaled Chehab, Jacksonville, FL (US); Eric R. Ritchey, Pearland, TX (US); Lisa A. Jones-Jordan, Worthington, OH (US); Loraine T. Sinnott, Columbus, OH (US); Xu Cheng, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/876,308

(22) Filed: Jan. 22, 2018

(65) Prior Publication Data

US 2018/0140181 A1    May 24, 2018

Related U.S. Application Data

(62) Division of application No. 15/007,660, filed on Jan. 27, 2016, now Pat. No. 10,042,181.

(51) Int. Cl.
*G02C 7/02* (2006.01)
*A61B 3/00* (2006.01)
(Continued)

(52) U.S. Cl.
CPC ............ *G02C 7/027* (2013.01); *A61B 3/0025* (2013.01); *A61B 3/0033* (2013.01);
(Continued)

(58) Field of Classification Search
CPC ....... A61B 3/0025; A61B 3/0033; A61B 3/10; A61B 3/103; A61B 3/0058;
(Continued)

(56) References Cited

U.S. PATENT DOCUMENTS 6,045,578 A    4/2000 Collins
6,626,538 B1   9/2003 Arrowsmith
(Continued)

FOREIGN PATENT DOCUMENTS

EP    1154302      11/2001
EP    1967892 A1   9/2008
(Continued)

OTHER PUBLICATIONS

Mutti D. O. et al., Refractive error, axial length, and relative peripheral refractive error before and after the onset of myopia. *Invest Ophthalmol Vis Sci*, Jun. 30, 2007, vol. 48, No. 6, pp. 2510-2519.

(Continued)

*Primary Examiner* — Jordan M Schwartz

(57) ABSTRACT

A method for estimating and tracking refractive error progression of an individual includes estimating a percentile of Spherical Equivalent Refraction (SPHEQ) as a function of at least the individual's age by comparison to a reference population; estimating an expected SPHEQ trajectory over a future predetermined period of time; comparing the expected SPHEQ trajectory with the reference population; and comparing the expected SPHEQ trajectory with an expected SPHEQ trajectory using an ametropia control treatment, thereby showing a possible treatment benefit over the predetermined period of time.

1 Claim, 11 Drawing Sheets

(51) Int. Cl.
*G02C 7/04* (2006.01)
*A61B 3/103* (2006.01)
*G16H 50/50* (2018.01)
*G16H 20/00* (2018.01)
*G16H 50/70* (2018.01)

(52) U.S. Cl.
CPC ............ *A61B 3/0058* (2013.01); *A61B 3/103* (2013.01); *G02C 7/024* (2013.01); *G02C 7/04* (2013.01); *G16H 50/50* (2018.01); *G02C 2202/24* (2013.01); *G16H 20/00* (2018.01); *G16H 50/70* (2018.01)

(58) Field of Classification Search
CPC .... G02C 2202/24; G02C 7/024; G02C 7/027; G02C 7/028; G02C 7/04; G02C 7/06
See application file for complete search history.

(56) References Cited

U.S. PATENT DOCUMENTS

| | | |
|---|---|---|
| 9,763,568 B2 | 9/2017 | Drobe |
| 2002/0154270 A1 | 10/2002 | Halpern |
| 2008/0062380 A1* | 3/2008 | Phillips .................. G02C 7/027 351/159.05 |
| 2010/0091242 A1* | 4/2010 | Baglini .............. A61B 5/04842 351/205 |
| 2012/0182520 A1 | 7/2012 | Neitz |
| 2014/0104563 A1* | 4/2014 | Bakaraju ................ G02C 7/061 351/159.41 |
| 2015/0124212 A1 | 5/2015 | Loertscher |
| 2016/0054588 A1 | 2/2016 | Brennan et al. |
| 2016/0338947 A1* | 11/2016 | Leahy .................. A61K 9/0051 |

FOREIGN PATENT DOCUMENTS

| | | |
|---|---|---|
| EP | 3199097 | 8/2017 |
| JP | 5667730 B1 | 12/2014 |
| KR | 2016006893 | 6/2016 |
| WO | WO2014050879 A1 | 4/2014 |
| WO | WO 2015070092 A1 | 5/2015 |
| WO | WO2015087435 | 6/2015 |

OTHER PUBLICATIONS

Saw S.-M. et al., Epidemiology of myopia. *Epidemiologic Rev*, Jan. 1, 1996, vol. 18, No. 2, pp. 175-187.
European Search Report for corresponding EPA No. 17153507.3 dated Jul. 28, 2017.
European Search Report for corresponding EPA No. 18168950.6 dated Sep. 27, 2018.

* cited by examiner

Scenario 1

Projections for age 9 for a child of age 8 with SPHEQ=-1

Scenario 2

Projections for age 9 for a child of age 8 with SPHEQ=-1 and rate of change of 0.5

Projections for age 9 for a child of age 8 with SPHEQ=-1 and rate of change of 1.5

Scenario 1

Projections for age 10 for a child of age 8 with SPHEQ=-1

Scenario 2

Projections for age 10 for a child of age 9 with SPHEQ=-1 and rate of change of 0.5    Projections for age 10 for a child of age 9 with SPHEQ=-1 and rate of change of 1.5

Myopia Track of a Subject with -1 D SPHEQ at Age 8.

Myopia Track of a Subject with -1 D SPHEQ at Age 9.

Myopia Track of a Subject with -1 D SPHEQ at Age 10.

AMETROPIA TREATMENT TRACKING METHODS AND SYSTEM

CROSS REFERENCE TO RELATED APPLICATION

The present application is a divisional application of U.S. patent application Ser. No. 15/007,660 filed on Jan. 27, 2016.

BACKGROUND OF THE INVENTION

Field of the Invention

The present invention relates to methods and a system for ametropia tracking, and more particularly, for myopia control treatment tracking.

The tracking methods and system estimate the potential refractive error of an individual over a future predetermined period of time based upon, for example, demographic data and/or myopia control treatment option. The tracking methods and system allow Eye Care Providers (ECPs) to demonstrate and track the effectiveness of treatments to slow the progression of myopia and allow individuals to understand the long-term benefit of a myopia control treatment.

Discussion of the Related Art

Common conditions which lead to reduced visual acuity include myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus light in front of the retinal plane and hyperopic eyes focus light behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow long enough.

Myopia has a high prevalence rate in many regions of the world. Of greatest concern with this condition is its possible progression to high myopia, for example, greater than five (5) or six (6) diopters, which dramatically affects one's ability to function without optical aids. High myopia is also associated with an increased risk of retinal disease, cataract, and glaucoma.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or intended to address symptoms.

Most eyes do not have simple myopia or hyperopia, but have myopic astigmatism or hyperopic astigmatism. Astigmatic errors of focus cause the image of a point source of light to form as two mutually perpendicular lines at different focal distances. In the following discussion, the terms myopia and hyperopia are used to include simple myopia and myopic astigmatism and hyperopia and hyperopic, astigmatism respectively.

Emmetropia describes the state of clear vision where an object at infinity is in relatively sharp focus with the crystalline lens relaxed. In normal or emmetropic adult eyes, light from both distant and close objects passing through the central or paraxial region of the aperture or pupil is focused by the crystalline lens inside the eye close to the retinal plane where the inverted image is sensed. It is observed, however, that most normal eyes exhibit a positive longitudinal spherical aberration, generally in the region of about +0.5 Diopters (D) for a 5 mm aperture, meaning that rays passing through the aperture or pupil at its periphery are focused +0.5 D in front of the retinal plane when the eye is focused to infinity. As used herein the measure D is the dioptric power, defined as the reciprocal of the focal distance of a lens or optical system, in meters.

The spherical aberration of the normal eye is not constant. For example, accommodation (the change in optical power of the eye derived primarily through changes to the crystalline lens) causes the spherical aberration to change from positive to negative.

U.S. Pat. No. 6,045,578 discloses that the addition of positive spherical aberration on a contact lens will reduce or control the progression of myopia. The method includes changing the spherical aberration of an ocular system to alter the growth in eye length. In other words, emmetropization may be regulated by spherical aberration. In this process, the cornea of a myopic eye is fitted with a lens having increasing dioptric power away from the lens center. Paraxial light rays entering the central portion of the lens are focused on the retina of the eye, producing a clear image of an object. Marginal light rays entering the peripheral portion of the cornea are focused in a plane between the cornea and the retina, and produce positive spherical aberration of the image on the latter. This positive spherical aberration produces a physiological effect on the eye which tends to inhibit growth of the eye, thus mitigating the tendency for the myopic eye to grow longer.

There remains a need to estimate the potential refractive error of an individual over a future predetermined period of time in order to demonstrate and track the effectiveness of myopia control treatments. There is also a need to give ECPs, parents, and patients a better understanding of the possible long-term benefit of a particular myopia control treatment.

SUMMARY OF INVENTION

The present invention overcomes the limitations of the prior art by providing methods that allow for estimating myopia progression over a future period of time, while also demonstrating and tracking the effectiveness of treatments to slow the progression of myopia.

In accordance with one aspect of the present invention, a method for estimating and tracking refractive error progression of an individual is provided. A percentile of Spherical Equivalent Refraction (SPHEQ) as a function of at least the individual's age is estimated by comparison to a reference population. An expected SPHEQ trajectory over a future predetermined period of time is estimated. The expected SPHEQ trajectory is compared with the reference population. The expected SPHEQ trajectory is compared with an expected SPHEQ trajectory using an ametropia control treatment, thereby showing a possible treatment benefit over the predetermined period of time.

In accordance with another aspect of the present invention, a method includes measuring actual SPHEQ refraction history for an individual while using a given ametropia control treatment, comparing to a reference population, and estimating an updated expected SPHEQ trajectory, thereby showing actual treatment benefit over a predetermined period of time.

In accordance with one aspect of the present invention, the ametropia control treatment may comprise a myopia control ophthalmic lens, for example, a myopia control contact lens.

In accordance with another aspect of the present invention, a method includes displaying a comparison of an expected SPHEQ trajectory with an expected SPHEQ trajectory using an ametropia control treatment.

In accordance with one aspect of the present invention, a system for estimating and tracking refractive error progression of an individual is provided. A server estimates an expected SPHEQ trajectory over a future predetermined period of time and an expected SPHEQ trajectory using a myopia control treatment. At least one database stores data from the server. A smart device in communication with the server via a network has a graphical user interface that displays a comparison of the expected SPHEQ trajectory over a future predetermined period of time with the expected SPHEQ trajectory using a myopia control treatment.

An object of the present invention is to provide an easy-to-use and reliable way for estimating myopia progression over a given period of time according to the type of ophthalmic lens a child may be using. Probabilities of faster or slower progression around a predicted refractive trajectory may also be presented.

Another object of the present invention is to help an ECP or parent choose a type of myopia control treatment and/or ophthalmic lens for a child by indicating the anticipated progression of myopia according to a specific type of myopia control treatment option.

Another object of the present invention is to monitor the effectiveness of a myopia progression control treatment.

Yet another object of the present invention is to provide methods that track myopia relative to a reference population based on at least one of country, region, gender, ethnicity, parental history, or other demographic or environmental factors relevant to myopia progression.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF INVENTION

Figure 1:
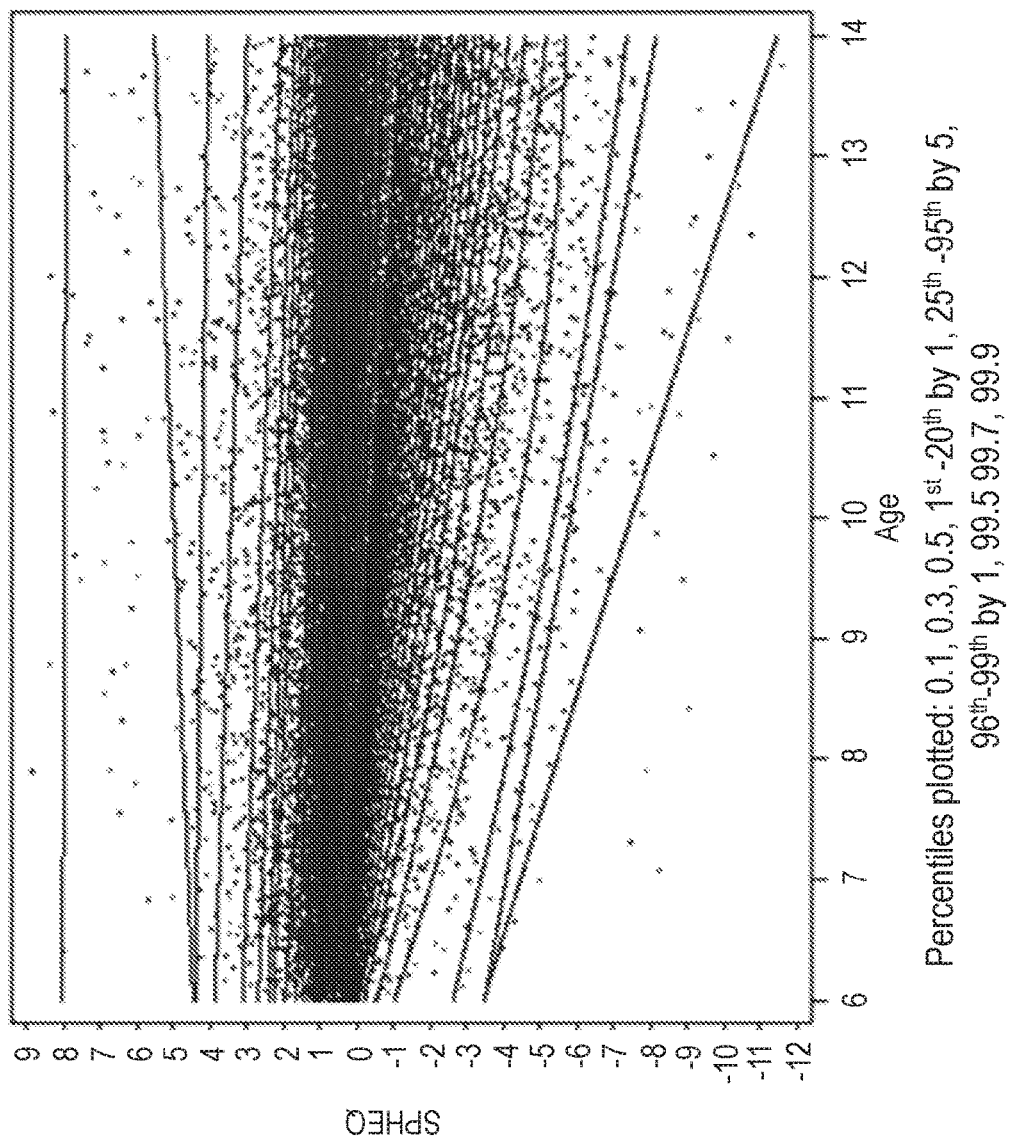
FIG. 1 displays a subset of fitted percentile curves to Spherical Equivalent Refraction (SPHEQ) values from a selected dataset for children between age 5.5 and 14.5.

The present invention relates to methods and a system for ametropia tracking, and more particularly, for myopia treatment tracking. The tracking methods and system estimate a potential refractive error of an individual over a future predetermined period of time relative to reference population, which 1) allow ECPs to predict and track refractive progression as well as demonstrate and track the effectiveness of treatments to slow the progression of myopia and/or 2) allow patients or parents to understand the long-term benefit of a myopia control treatment.

Although the discussion below is directed to myopia, the present invention is not so limited and could be applied to other refractive errors, such as hyperopia or astigmatism. In addition, the discussion below is directed to tracking methods for individuals, in particular children having an approximate age of 6 to 14. However, the tracking methods could also be applied to younger children, older adolescents, or young adults depending on available datasets.

According to the present invention, a method for estimating and tracking a potential refractive error progression of a child comprises: estimating a percentile of Spherical Equivalent Refraction (SPHEQ) as a function of at least a child's age by comparison to a reference population; estimating an expected SPHEQ trajectory over a future predetermined period of time; comparing the expected SPHEQ trajectory with the reference population; and comparing the expected SPHEQ trajectory with an expected SPHEQ trajectory using a myopia control treatment, thereby showing the possible treatment benefit over the predetermined period of time.

A. Estimating a Percentile SPHEQ Relative to a Reference Population

According to the present invention, a percentile of Spherical Equivalent Refraction (SPHEQ) is determined as a function of at least a child's age by comparison to a reference population. A child is at the pth percentile of SPHEQ population reference percentiles if p % of children have SPHEQ values no more than the SPHEQ of the child.

In order to estimate the reference population percentiles, a selected dataset is utilized. According to the present invention, the Collaborative Longitudinal Evaluation of Ethnicity and Refractive Error (CLEERE) dataset or subset thereof may be used to estimate percentiles of SPHEQ as a function of age and ethnicity. For example, a selected dataset may include all CLEERE observations for children having an age between 5.5 and 14.5 years and an ethnicity of White, Black, Hispanic, Asian, or Native American.

The selected dataset is modeled to obtain reference population percentile curves. According to a specific embodiment of the present invention, reference population percentile curves between 0.1 and 99.9 in increments of 0.1 may be fit using, for example, PROC QUANTREG from SAS®. The 0.1-0.4 and 94.6-99.9 percentile curves may be fit with linear models in age; the 0.5-4.5 and 45.6-94.5 percentile curves may be fit with quadratic models in age; and the 4.6-45.5 percentile curves may be fit with cubic models in age. These variants in model complexity may result from pruning higher order polynomial terms that may not be statistically significant. It will be appreciated that other models and other increments may be utilized. Also other platforms, e.g. the CRAN package GAMLSS (Generalized Additive Models for Location, Scale, and Shape), may be used to fit reference population percentile curves.

FIG. 1 displays a set of the modeled reference population percentile curves in which the SPHEQ values as a function of age from the selected CLEERE dataset are superimposed.

It should be noted that the distribution of ethnicity in a selected CLEERE sample may not match that of the United States. When proportions in sample strata do not coincide with proportions in a reference population of interest, estimates provided by the data may be biased. Bias can be corrected through weights that are specific to each stratum. The general form of the weight is (Nk/N)/(nk/n), where k indexes the strata, N represents the population size, Nk represents the population stratum size, n represents the sample size, and nk represents the sample stratum size. This form of weighting may be used to make the distribution of ethnicities in a CLEERE sample more comparable to that of the United States. For the U.S. population, ethnicity proportions (the Nk/N) may come from: http://www.childstats.gov/americaschildren/tables/pop3.asp It will be appreciated that other comparable datasets or subsets of CLEERE may be selected to provide data needed for other reference populations, for example, keyed to or based on at least one of country, region, gender, ethnicity, or parental history. Examples of existing dataset(s) that may be used in conjunction with the CLEERE dataset are Singapore Cohort of the Risk factors for Myopia (SCORM); Sydney Myopia Study (SMS) and the Sydney Adolescent Vascular Eye Disease Study (SAVES); Northern Ireland Childhood Errors of Refraction (NICER); or Anyang Childhood Eye Study (Anyang).

According to another embodiment of the present invention, a Spherical Equivalent Refraction (SPHEQ) may be estimated as a function of input data. The input data may be one or more selected from the group consisting of: age; age of first optical refraction; current and/or prior year dry refraction value; current and/or prior year dry retinoscopy; current and/or prior year dry autorefraction; current and/or prior year cycloplegic manifest refraction; current and/or prior year cycloplegic retinoscopy; current and/or prior year cycloplegic autorefraction; gender; race and/or ethnic group; country of residence; urban or rural address; number of myopic parents; number of myopic siblings; level of close work activity (e.g., number of reading hours per day or week or month); level of outdoor activity (e.g., number of hours spent out door per day, or week or month); current and/or prior year axial length; current type of myopia correction and/or myopia progression prevention being used; other demographic or environmental variables considered relevant to refractive progression; and alternative correction or prevention options.

Thus, a percentile of Spherical Equivalent Refraction (SPHEQ) for a specific child can be estimated by comparing his or her measured SPHEQ relative to the modeled reference population percentile curves.

B. Estimating Expected SPHEQ/Percentile Values and Trajectory

The selected dataset used to estimate the SPHEQ reference population percentiles may also be used to estimate expected SPHEQ trajectories or projections over a future predetermined period of time (e.g., expected future SPHEQ values at year k+1 or k+n, wherein n is an integer).

In a specific embodiment of the present invention, the selected dataset may be used to fit a first model of SPHEQ at year k+1 as a function of baseline/current age and baseline SPHEQ at year k (Scenario 1). A second model of SPHEQ at year k+1 may be fit using baseline/current age, baseline SPHEQ at year k, and past history of SPHEQ (Scenario 2). For past history, measured spherical equivalent rate of change between year k and k−1 (progression rate) may be utilized. Scenario 1 and/or Scenario 2 may include a random effect to account for the correlation in repeated measures from the same subject. The models may be fit by PROC GLIMMIX of SAS® using linear regression with a random effect. It will be appreciated that other models and fitting platforms, such as R, may be utilized.

To estimate the distribution of prediction error around expected values, error distributions (probabilities) may be obtained by the method disclosed in Jiang et al., *Distribution-free Prediction Intervals in Mixed Linear Models*, Statistica Sinica, 12(2002), 537-553.

Figure 2A:
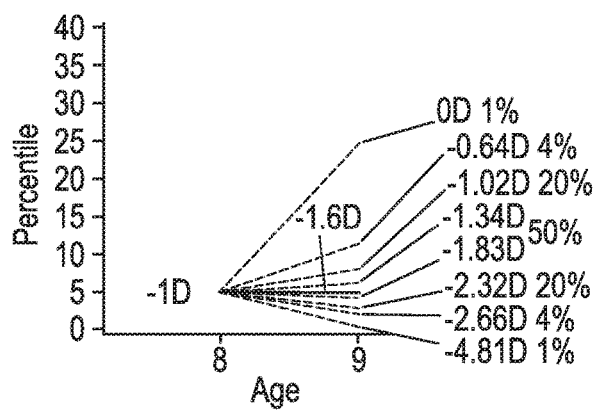
FIGS. 2A-2B graphically display percentile projections for a 9-year-old who, at age 8, had a spherical Equivalent Rx (SPHEQ) of −1.0D. Scenario 1 is represented in FIG. 2A and Scenario 2 is represented in FIG. 2B.
Figure 2B:
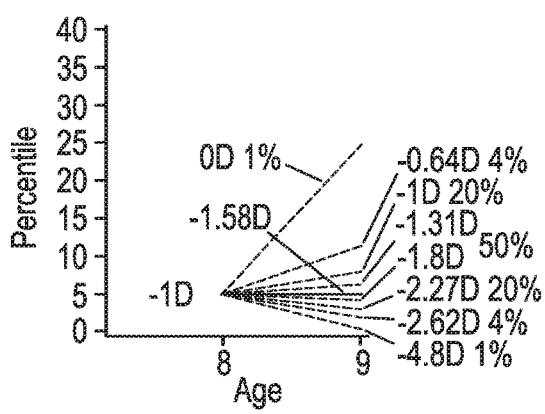
Figure 2B:
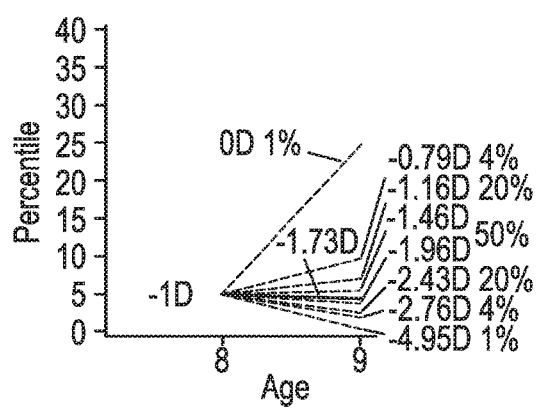
Figure 3A:
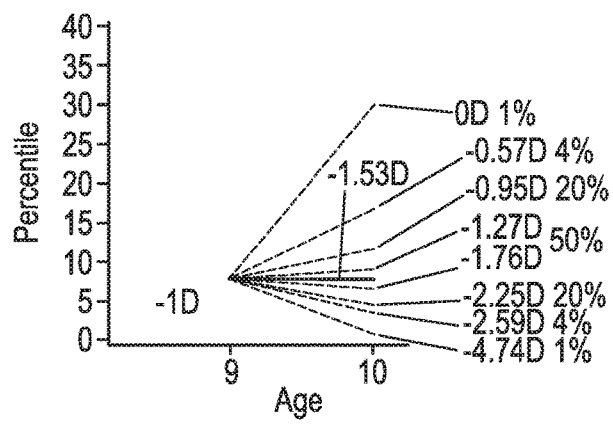
FIGS. 3A-3B graphically display percentile projections for a 10-year-old who, at age 9, had a spherical Equivalent Rx (SPHEQ) of −1.0D. Scenario 1 is represented in FIG. 3A and Scenario 2 in represented in FIG. 3B.
Figure 3B:
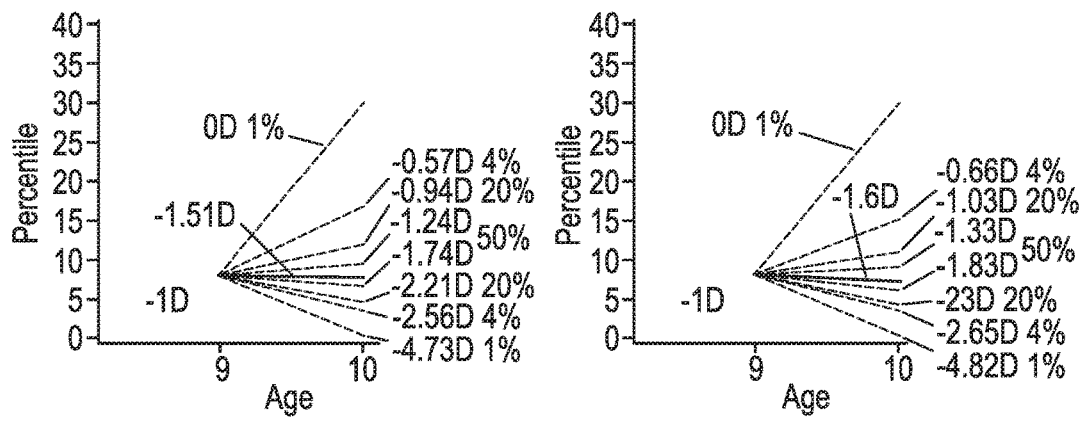
Figure 4A:
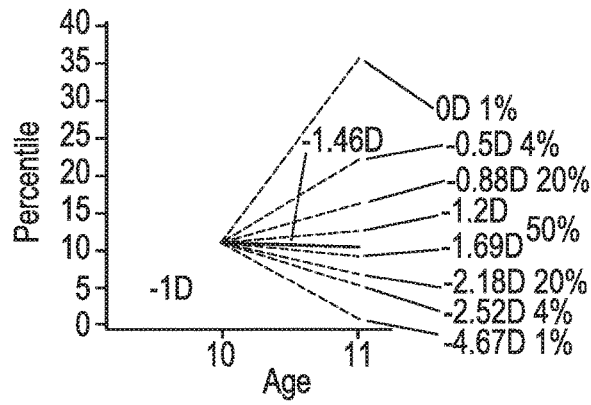
FIGS. 4A-4B graphically display percentile projections for an 11-year-old who, at age 10, had a spherical Equivalent Rx (SPHEQ) of −1.0D. Scenario 1 is represented in FIG. 4A and Scenario 2 is represented in FIG. 4B.
Figure 4B:
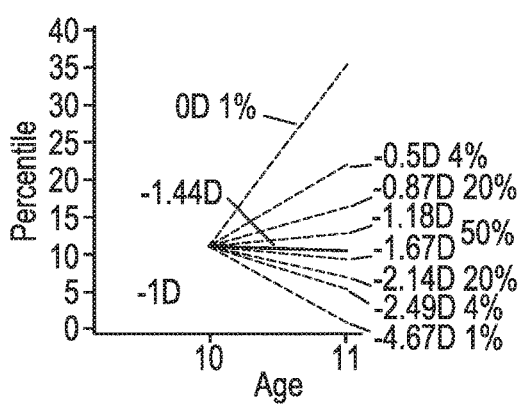
Figure 4B:
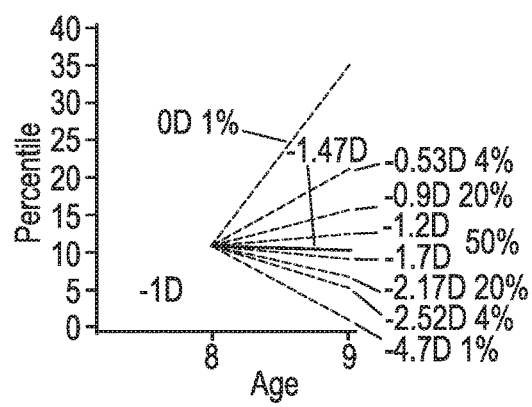

FIGS. 2A-4B graphically display the expected SPHEQ/percentile values at year k+1 for a child with baseline age 8 (FIGS. 2A-2B); age 9 (FIGS. 3A-3B), or age 10 (FIGS. 4A-4B) and a baseline SPHEQ of −1.0D. For each baseline age, Scenario 1 projections are in the first panel (FIGS. 2A, 3A, and 4A). Scenario 2 projections are in two panels, with a rate of change of 0.5D shown on the left and 1.5D shown on the right (FIGS. 2B, 3B, and 4B).

FIGS. 2A-2B graphically display expected SPHEQ/percentile values for a 9-year-old who, at age 8, had a baseline SPHEQ of −1.0D. Scenario 1 (FIG. 2A) is represented in the top panel and Scenario 2 (FIG. 2B) in the bottom panel. The baseline SPHEQ of −1.0D is the 5.1 percentile of age 8 SPHEQ values.

In FIG. 2A, the expected SPHEQ at age 9 is −1.6D, which is the 4.9 percentile. The solid line connects the baseline and expected SPHEQ value. Prediction error intervals are provided by the endpoints of the dashed lines. The column of percentages on the far right of the panel indicates the probability that an expected future outcome lies in the interval to the left of the percent. For example, there is a chance of 50% that the next year's SPHEQ will be between −1.8D and −1.3D, which at age 9 is the 4.2 and 6.1 percentile, respectively. There is a chance of 90% that the next year's SPHEQ will be between −2.3D and −1.0D which at age 9 is the 7.9 and 2.8 percentile, respectively.

In FIG. 2B, two examples are shown for the same subject as in FIG. 2A, but with the rate of change taken into account. On the left, the rate of change is 0.5D and on the right the rate of change is 1.5D. In the case of the 0.5D rate of change, there is a chance of 90% that the next year's SPHEQ will be between −2.3D and −1.0D which is the 3.0 and 8.0 percentile, respectively. In the case of the 1.5D rate of change, there is a chance of 90% that the next year's SPHEQ will be between −2.4D and −1.2D which is the 2.6 and 7.0 percentile, respectively.

90% that the next year's SPHEQ will be between −2.1D and −1.0D. In the case of the 1.5D rate of change, there is a chance of 90% that the next year's SPHEQ will be between −2.2D and −1.0D.

| Example | Subject Age (years) | Subject Baseline Refraction (D) | Current percentile relative to population, at current age and Rx | Population 50th percentile Rx | Most Likely Projection Percentile at current age +1 year | Probability and Projection of Refraction (D) at current age +1 year | Probability and Projection of Refraction (D) at current age +1 year with a 0.5 D rate of change | Probability and Projection of Refraction (D) at current age +1 year with a 1.5 D rate of change |
|---|---|---|---|---|---|---|---|---|
| 1 (FIGS. 2A-2B) | 8 | −1.00 | 5.1% | 0.63 D | 4.9% | Most likely −1.6 D 50% chance of −1.3 D to −1.8 D 90% chance of no progression to −2.2 D | Most likely −1.6 D 50% chance of −1.3 D to −1.8 D 90% chance of no progression to −2.3 D | Most likely −1.7 D 50% chance of −1.5 D to −2.0 D 90% chance of −1.2 D to −2.4 D |
| 2 (FIGS. 3A-3B) | 9 | −1.00 | 8.1% | 0.51 D | 7.7% | Most likely −1.5 D 50% chance of −1.3 D to −1.8 D 90% chance of no progression to −2.3 D | Most likely −1.5 D 50% chance of −1.2 D to −1.7 D 90% chance of no progression to −2.2 D | Most likely −1.6 D 50% chance of −1.3 D to −1.8 D 90% chance of no progression to −2.3 D |
| 3 (FIGS. 4A-4B) | 10 | −1.00 | 11.2% | 0.41 D | 10.6% | Most likely −1.5 D 50% chance of −1.2 D to −1.7 D 90% chance of no progression to −2.2 D | Most likely −1.4 D 50% chance of −1.2 D to −1.7 D 90% chance of no progression to −2.1 D | Most likely −1.5 D 50% chance of −1.2 D to −1.7 D 90% chance of no progression to −2.2 D |

FIGS. 3A-3B graphically display expected SPHEQ/percentile values for a 10-year-old who, at age 9, had a SPHEQ of −1.0D. Scenario 1 is represented in FIG. 3A and Scenario 2 is represented in FIG. 3B. A baseline SPHEQ of −1.0D is the 8.1 percentile of age 9 SPHEQ values.

In FIG. 3A, the expected SPHEQ is −1.5D, which at age 10 is the 7.7 percentile. There is a chance of 50% that the next year's SPHEQ will be between −1.8D and −1.3D which at age 10 is the 6.6 and 9.3 percentile, respectively. There is a chance of 90% that the next year's SPHEQ will be between −2.3D and −1.0D, which at age 10 is the 4.6 and 11.7 percentile, respectively.

In FIG. 3B, two examples are shown for the same subject as in FIG. 3A, but with the rate of change taken into account. In the case of the 0.5D rate of change, there is a chance of 90% that the next year's SPHEQ will be between −2.2D and −0.9D which at age 10 is the 4.7 and 11.9 percentile, respectively. In the case of the 1.5D rate of change, there is a chance of 90% that the next year's SPHEQ will be between −2.3D and −1.0D which at age 10 is the 4.4 and 11 percentile, respectively.

FIGS. 4A-4B graphically display expected SPHEQ/percentile values for an 11-year-old who, at age 10, had a SPHEQ of −1.0D. Scenario 1 is represented in FIG. 4A and Scenario 2 is represented in FIG. 4B. A baseline SPHEQ of −1.0D is the 11.2 percentile of age 10 SPHEQ values.

In FIG. 4A, the expected SPHEQ is −1.5D, which at age 10 is the 10.6 percentile. There is a chance of 50% that the next year's SPHEQ will be between −1.7D and −1.2D. There is a chance of 90% that the next year's SPHEQ will be between −2.2D and −1.0D.

Figure 5A:
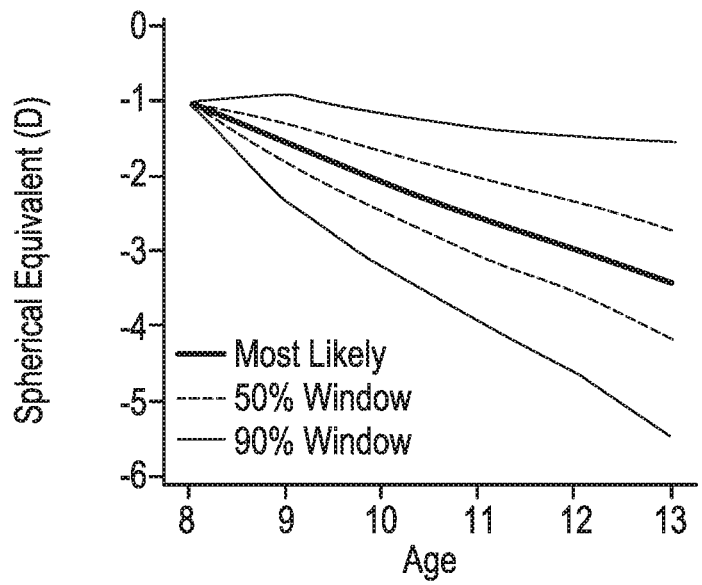
FIGS. 5A-5C graphically display SPHEQ projections for an 8, 9, and 10 year old child with a spherical equivalent Rx (SPHEQ) of −1.0D for 5 years (or to age 14). Also shown are the 50% and 90% SPHEQ confidence windows.
Figure 5B:
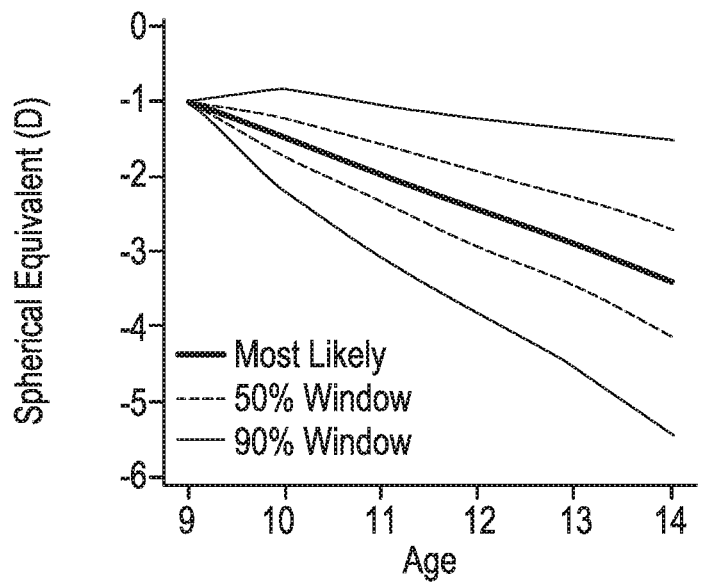
Figure 5C:
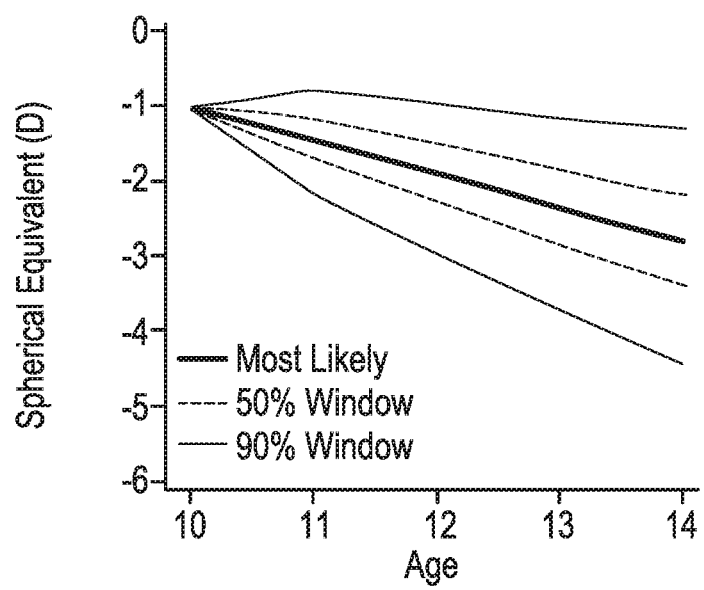

In FIG. 4B, two examples are shown for the same subject as in FIG. 4A, but with the rate of change taken into account. In the case of the 0.5D rate of change, there is a chance of FIGS. 5A-5C graphically display data similar to that shown in FIGS. 2A-4B, but directed to SPHEQ trajectory extended over 5 years period from baseline age (or up to the age of 14). The SPHEQ trajectories or projections are shown as a function of SPHEQ and age with 50% and 90% prediction or confidence windows.

C. Comparing Expected SPHEQ Trajectories to Reference Population

According to an exemplary embodiment of the present invention, an expected SPHEQ trajectory may be compared to the reference population percentiles for illustration and tracking.

Figure 6:
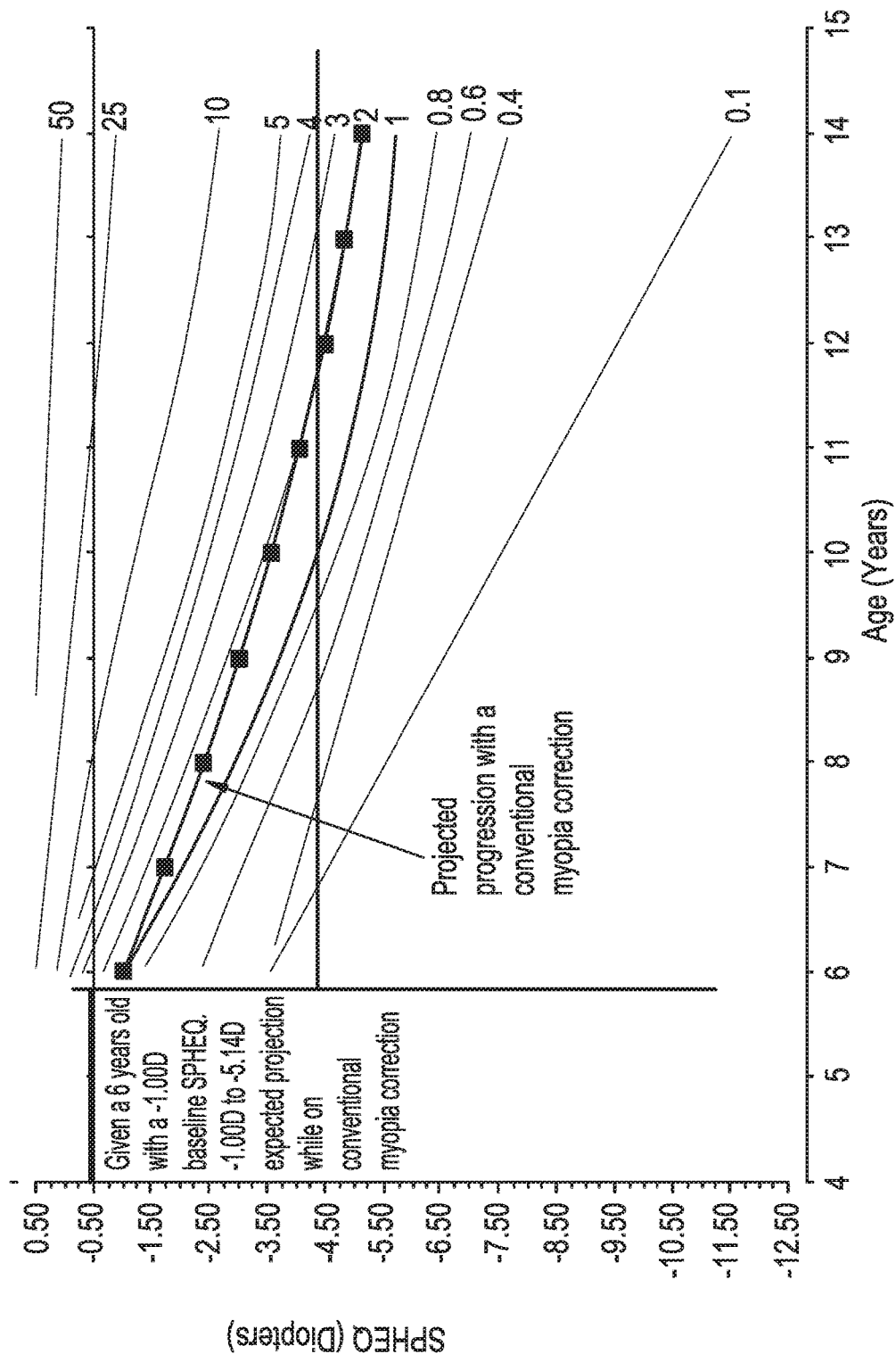
FIG. 6 graphically displays an expected trajectory for a 6-year-old who, at age 7, is projected to have a SPHEQ between −1.14D to −2.45D with 90% confidence using conventional myopia correction. The expected trajectory continues to age 14, with an expected SPHEQ of −5.14D. The expected trajectory is superimposed on a subset of percentiles curves ranging from the 0.1 to the 50th percentile.

FIG. 6 shows an expected SPHEQ trajectory for a baseline −1.0D SPHEQ of a 6 year old, who at age 7, is projected to have a SPHEQ of −1.73D with a 90% prediction interval of −1.1D to −2.4D. The expected SPHEQ trajectory is superimposed over a subset of percentiles curves from FIG. 1 ranging from the 0.1 to the 50th percentile. The expected trajectory continues to age 14, with an expected SPHEQ of −5.14D.

Because a conventional myopia correction does not treat myopia progression, FIG. 6 would help ECPs and parents visualize the long-term impact of myopia progression and the likely endpoint relative to a population with the same initial SPHEQ percentile level.

D. Comparing Possible Impact of a Myopia Control Treatment

According to the present invention, an expected SPHEQ trajectory with conventional myopia correction may be compared to an expected SPHEQ trajectory using a myopia control treatment, thereby showing a possible treatment benefit over a predetermined period of time.

Figure 7:
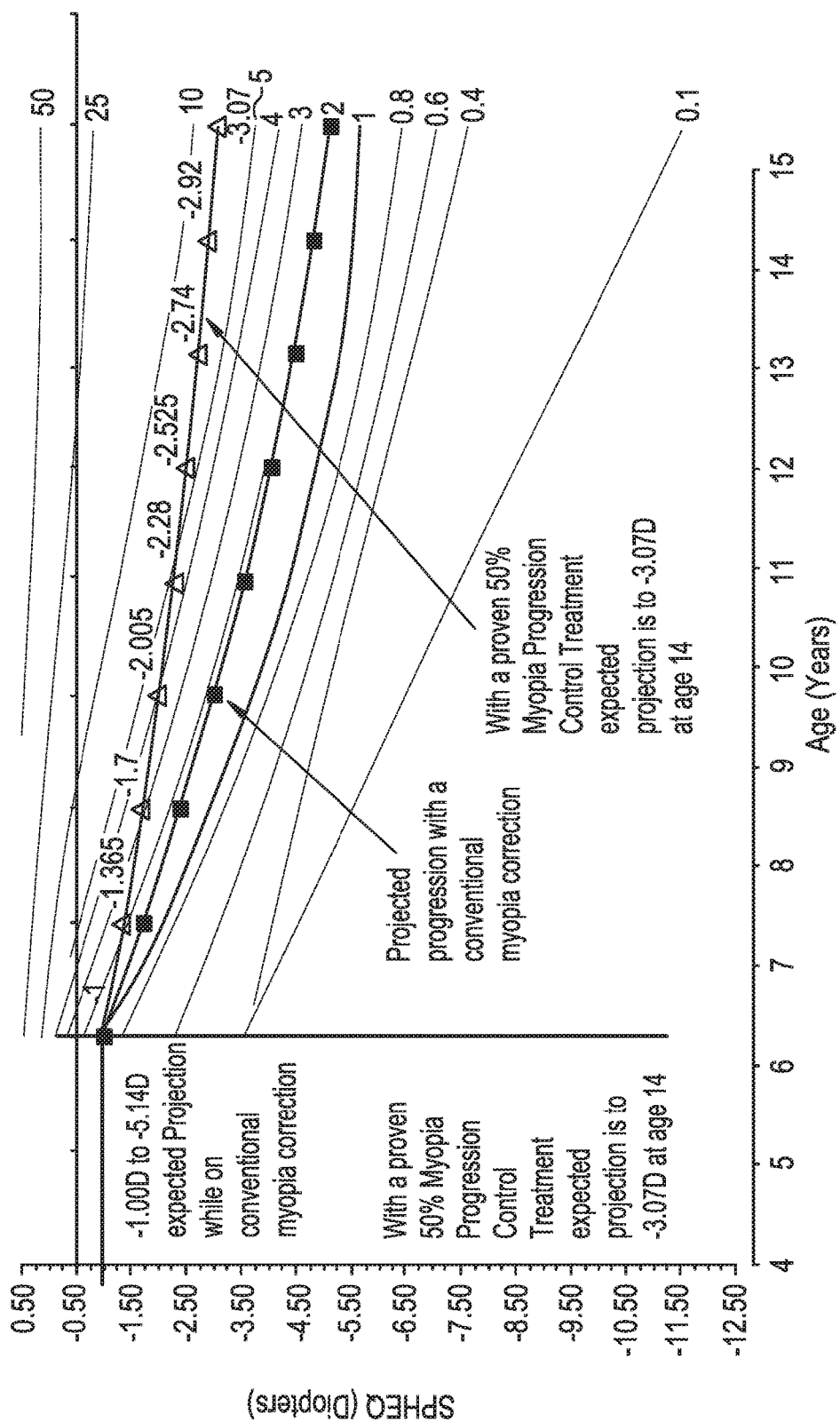
FIG. 7 shows FIG. 6 with an expected trajectory for a 6-year-old who, at age 14, is projected to have a SPHEQ of −3.07D using a myopia control treatment.

For example, an expected SPHEQ trajectory of a child continuing with conventional myopia correction (e.g., FIG. 6) may be compared to an expected SPHEQ trajectory using a myopia control treatment (e.g., FIG. 7). The myopia control treatment may be myopia control ophthalmic lenses, such as myopia control contact lenses. Other myopia control treatments may comprise optical, pharmaceutical, environmental, or other interventions. In a specific embodiment, data from myopia control treatments that have been clinically validated to deliver a 50% treatment efficacy may be used. It will be appreciated that values for other myopia control treatments and/or efficacies (e.g., 60% or 80%) may be utilized.

FIG. 7 shows the 1st percentile SPHEQ of a general population, which at age 6 is −1.0D and falls to −5.7D over the next 8 years. Also shown is the expected SPHEQ trajectory using a conventional myopia correction for a 6-year-old starting at −1.0D and progressing to −5.14D at age 14 years old. Finally shown is an expected SPHEQ trajectory for a child using a myopia control treatment beginning at age 6, with a SPHEQ of −1.0D and a projected SPHEQ of −3.07D at age 14. Thus, there is an expected reduction in the myopia endpoint at age 14 of more than 2D.

Accordingly, the methods and system of the present invention provide a visual representation of a child's myopia relative to a reference population at any age and provides a myopia progression perspective with conventional and/or myopia control treatment options, plus a potential SPHEQ endpoint based on age and/or other individual factors, such as the input data discussed above.

E. Estimating the Expected Impact of Myopia Control Treatment

According to the present invention, the most likely impact and benefit of a myopia control treatment may be estimated. For a given time interval, the actual SPHEQ refraction history for a child with a particular myopia control treatment may be measured. The expected SPHEQ trajectory may then be recalculated and compared to the initial expected SPHEQ trajectory and the reference population percentiles.

Figure 8:
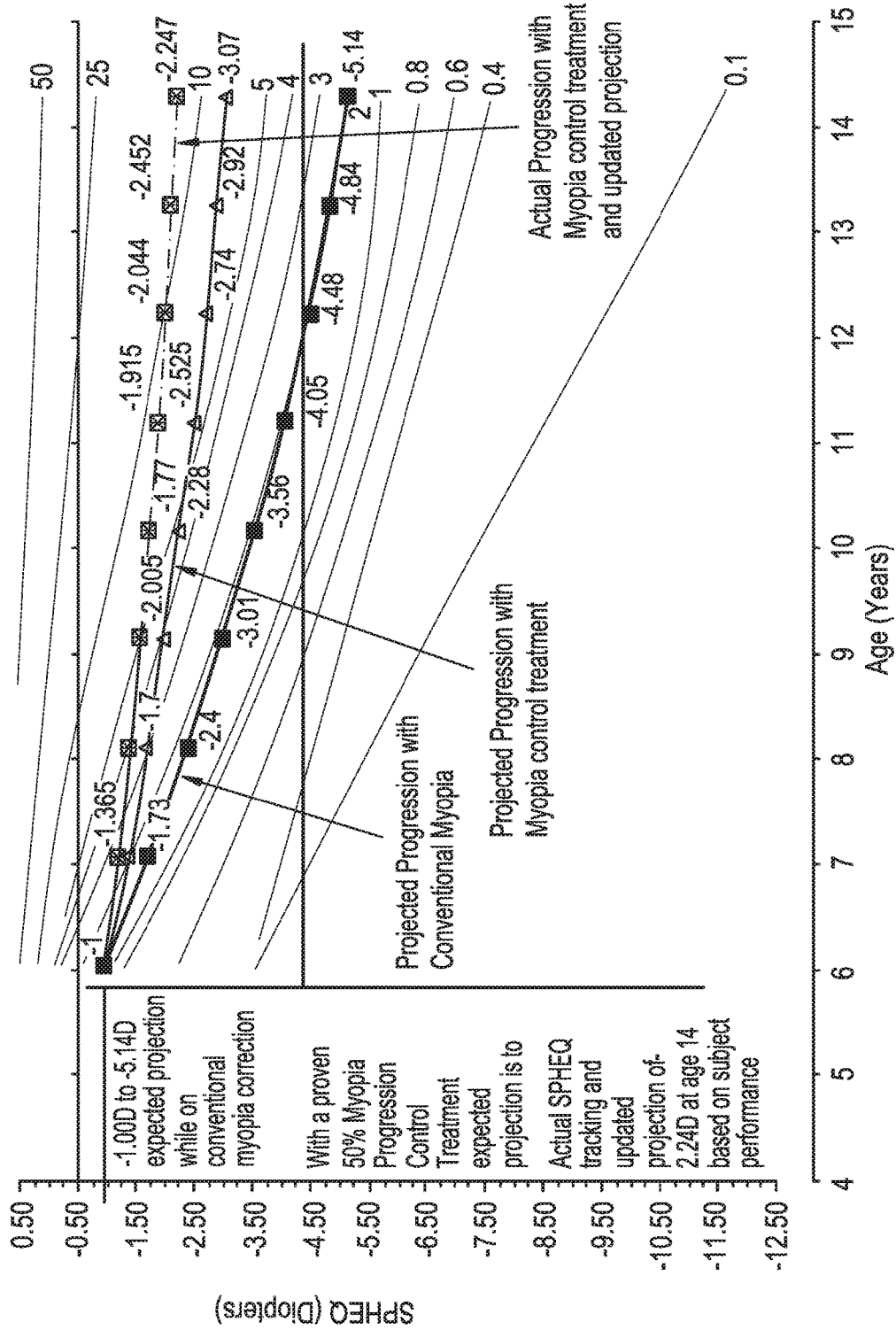
FIG. 8 shows tracked actual SPHEQ versus expected trajectories of conventional myopia correction and myopia control treatment for a 6-year-old who, at age 14, with a myopia control treatment is projected to have a SPHEQ of −2.24D based on an updated projection.

FIG. 8 is an illustration of the same child as in FIG. 7 with actual measured SPHEQ data showing a four year follow-up up to age 10 plotted in a solid line, thereby tracking of the actual SPHEQ history while using a myopia control treatment. In this example, the child's myopia control treatment performed better than the expected SPHEQ trajectory and resulted in a slowdown of 70% in the myopia rate of progression relative to a conventional myopia correction. Further, the dashed line is a representation of an updated expected SPHEQ trajectory based on the child's measured myopia progression rate. The child is projected to have a SPHEQ of −2.24D at age 14 based on the updated projection.

Thus, the present invention helps visualize the continued benefit of a myopia control treatment and helps ECPs manage customer or parent expectations. More importantly, the present invention may provide updates on the success or failure of a myopia control treatment option and a child's myopia progression relative to a reference population and an expected SPHEQ endpoint.

F. Additional Methods

As noted, the present invention helps visualize the treatment benefit of a selected myopia control treatment. Accordingly, the present invention allows the printing or displaying of any of Figures (e.g., FIGS. 6-8), input data, output data, or any combination thereof.

The input data may be as discussed above. The output data may be one or more selected from the group consisting of current percentile relative to a reference population; current deviation in diopters away from the 50th percentile refraction of a reference population; most likely SPHEQ percentile trajectory starting at current age and continuing to any given future age; most likely SPHEQ trajectory starting at current age and continuing to any given future age; for each future age, prediction intervals within which future observations are likely to fall with specified levels of confidence; expected SPHEQ percentile trajectory if a myopia control treatment is initiated at the current or a future age; expected SPHEQ refraction trajectory if a myopia control treatment is initiated at the current or a future age; refraction/percentile trajectories with prediction intervals; and projected and actual refraction/percentile trajectories with a myopia control treatment.

Thus, in particular, a comparison of an expected SPHEQ trajectory with an expected SPHEQ trajectory using a myopia control treatment can be printed or displayed. A printout or display may be in any suitable format, such as a table, graph, or pie chart. The display may be on a graphical user interface of a computer or of a smart device (e.g., a tablet computer, smart phone, personal digital assistant, wearable digital device, gaming device, TV). In a specific embodiment, the display may be synchronized on an Eye Care provider's computer or smart device and on a user computer or smart device.

The present invention allows for continuous monitoring of a child using a particular myopia control treatment. For example, the actual SPHEQ refraction history for a child while using a given myopia control treatment may be measured at periodic intervals (e.g., weekly, monthly, yearly). An updated expected SPHEQ trajectory is determined at each interval. Data comprising SPHEQ measurements, updated expected SPHEQ trajectory at each interval, and any input and/or output data may be saved to a secure server and/or database. The continuous monitoring may be for a plurality of children and for a plurality of myopia control treatments.

According to the present invention, an authorized user may be granted access to view the saved data, for example, via a weblink or software application (e.g., a downloadable app to smart device) that allows access to the secure server and/or database. An authorized user may include at least one of an Eye Care Provider, customer, parent, or child.

The saved data or a subset thereof may be utilized to establish a database comprising clinical data on efficacy of one or more myopia control treatments. In a particular embodiment, the saved data or subset thereof may be provided to a third party for ongoing data analysis. In this case, the data may be anonymous so that the privacy of children will be protected, for example, by using a numeric or alphanumeric identifier.

In an embodiment, data for children that have refused any myopia control treatment may be used to continually update one or more of the selected datasets discussed above, for example, the CLEERE dataset.

G. System and Computer Environment for Myopia Tracking

Figure 9:
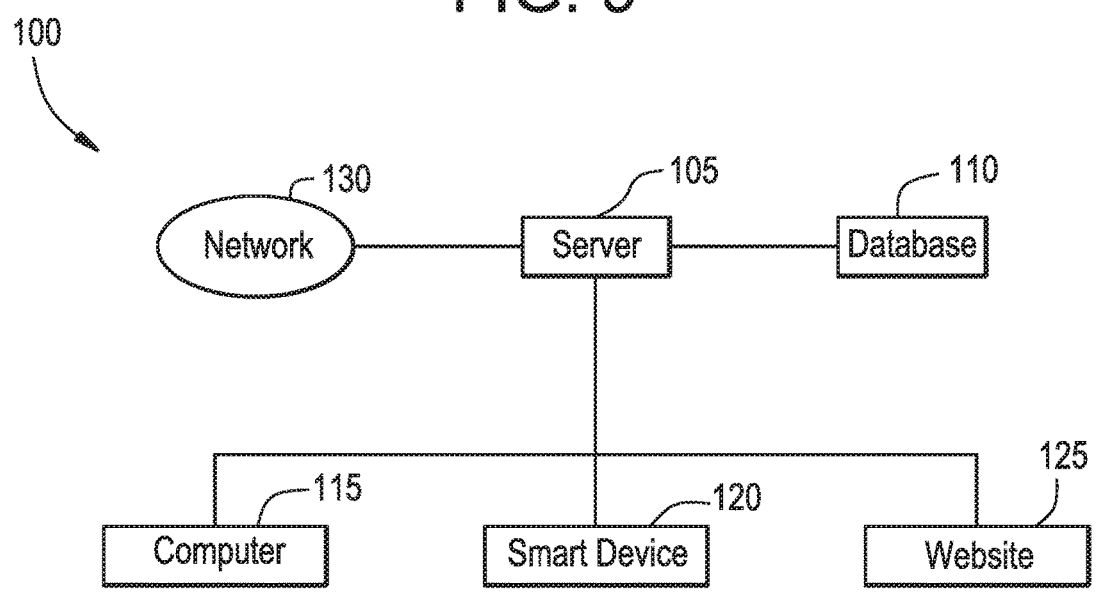
FIG. 9 shows a schematic diagram of a system according to an embodiment of the present invention.

The present invention is also directed to a system for myopia tracking. FIG. 9 is a schematic diagram of a system 100 according to an embodiment of the present invention. System 100 comprises a server 105 for receiving input data; for performing data analysis such as one or more of the steps discussed above, and for outputting data. The input data and output data may be stored or saved in at least one database 110. The input and/or output data may be accessed by a software application installed on computer 115 (for example a computer in the office of an ECP); by a downloadable software application (app) on a smart device 120; or by a secure website or weblink 125 accessible by a computer via network 130. The input and/or output data may be displayed on a graphical user interface of a computer or smart device.

In a specific embodiment, a system for estimating and tracking refractive error progression of an individual comprises a server for estimating an expected SPHEQ trajectory over a future predetermined period of time and an expected SPHEQ trajectory using a myopia control treatment; at least one database for storing data from the server; and a smart device in communication with the server via a network and comprising a graphical user interface for displaying a comparison of the expected SPHEQ trajectory over a future predetermined period of time with the expected SPHEQ trajectory using a myopia control treatment.

As will be appreciated by one skilled in the art based on this disclosure, aspects of the present invention may be embodied as a system, method, or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store a program for use by or in connection with an instruction execution system, apparatus, or device.

Computer program code for carrying out operations for aspects of the present invention may be written in any combination of one or more programming languages, including an object oriented programming language such as Java, Smalltalk, C++, C#, Transact-SQL, XML, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified.

These computer program instructions may also be stored in a computer readable medium that can direct a computer, other programmable data processing apparatus, or other devices to function in a particular manner, such that the instructions stored in the computer readable medium produce an article of manufacture including instructions which implement the functions/acts specified.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified.

Figure 10:
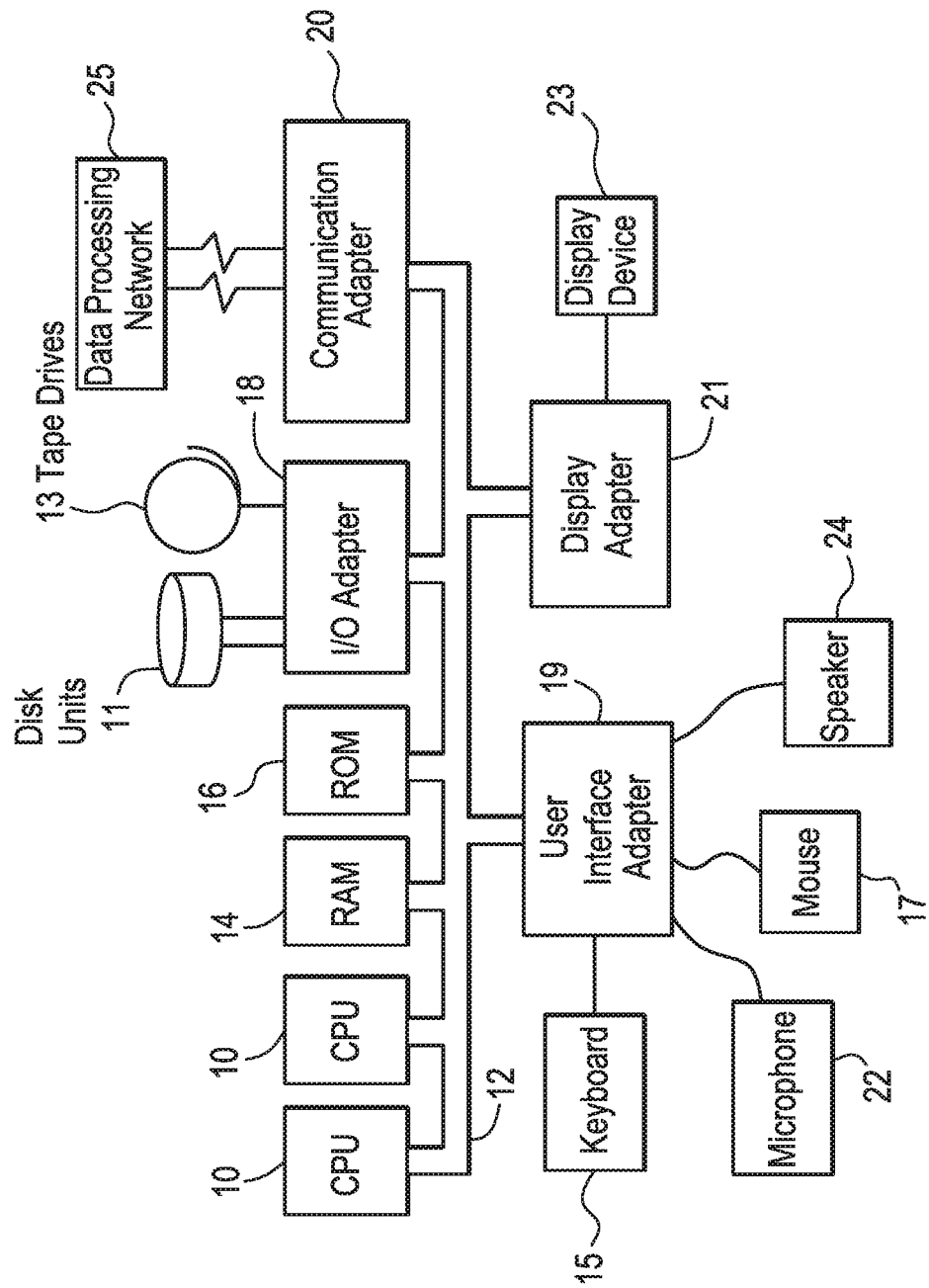
FIG. 10 shows a representative hardware environment for practicing at least one embodiment of the present invention.

Referring now to FIG. 10, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

As used herein, "in communication" includes physical and wireless connections that are indirect through one or more additional components (or over a network) or directly between the two components described as being in communication.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A computer-implemented method for estimating and tracking refractive error progression of an individual, comprising:

estimating a percentile of Spherical Equivalent Refraction (SPHEQ) as a function of the individual's age and at least one of country, region, gender, ethnicity, or parental history by comparison to a reference population by modeling data from a selected dataset;

estimating an expected SPHEQ trajectory of the individual over a future predetermined period of time using a predetermined set rate of change;

determining an expected SPHEQ trajectory using an ametropia control treatment;

displaying, on a graphic user interface, a comparison of the estimated expected SPHEQ trajectory of the individual with the expected SPHEQ trajectory using the ametropia control treatment;

displaying, on a graphic user interface, a comparison of the estimated percentile of SPHEQ with the estimated expected SPHEQ trajectory of the individual; and using the comparisons to estimate and track the refractive error progression of the individual.

* * * * *